United States Patent
Liu et al.

(10) Patent No.: US 10,562,828 B2
(45) Date of Patent: *Feb. 18, 2020

(54) STABILIZED DCD AND/OR ALKYL THIOPHOSPHORIC TRIAMIDE SOLVENT SYSTEMS AND USE IN AGRICULTURAL APPLICATIONS

(71) Applicant: RHODIA OPERATIONS, Paris (FR)

(72) Inventors: Hong Liu, Pennington, NJ (US); Jiamin Wu, Penndel, PA (US); Andre Gomes, Jackson, NJ (US); Krish Shanmuga, Plainsboro, NJ (US); Zhiyun Chen, Newtown, PA (US)

(73) Assignee: RHODIA OPERATIONS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/415,024

(22) Filed: May 17, 2019

(65) Prior Publication Data

US 2019/0270682 A1 Sep. 5, 2019

Related U.S. Application Data

(63) Continuation of application No. 15/637,110, filed on Jun. 29, 2017, now Pat. No. 10,336,660.

(60) Provisional application No. 62/356,035, filed on Jun. 29, 2016.

(51) Int. Cl.
| | |
|---|---|
| *C05C 1/00* | (2006.01) |
| *C05C 9/00* | (2006.01) |
| *C05G 3/08* | (2006.01) |
| *C05C 11/00* | (2006.01) |
| *C09K 15/18* | (2006.01) |
| *C05B 7/00* | (2006.01) |
| *C09K 15/12* | (2006.01) |
| *C05G 3/00* | (2006.01) |
| *C07F 9/22* | (2006.01) |
| *C09K 15/28* | (2006.01) |
| *C09K 15/32* | (2006.01) |

(52) U.S. Cl.
CPC .................. *C05G 3/08* (2013.01); *C05B 7/00* (2013.01); *C05C 1/00* (2013.01); *C05C 9/00* (2013.01); *C05C 11/00* (2013.01); *C05G 3/0064* (2013.01); *C07F 9/224* (2013.01); *C09K 15/12* (2013.01); *C09K 15/18* (2013.01); *C09K 15/28* (2013.01); *C09K 15/324* (2013.01); *Y02P 60/218* (2015.11)

(58) Field of Classification Search
None
See application file for complete search history.

(56) References Cited

U.S. PATENT DOCUMENTS

| | | |
|---|---|---|
| 2013/0145806 A1 | 6/2013 | Iannotta et al. |
| 2014/0090432 A1 | 4/2014 | McKnight et al. |
| 2014/0174140 A1 | 6/2014 | Ortiz-Suarez et al. |
| 2015/0143860 A1 | 5/2015 | McKnight et al. |
| 2015/0218060 A1 | 8/2015 | Hayes |
| 2016/0107947 A1 | 4/2016 | McKnight et al. |
| 2016/0332929 A1* | 11/2016 | McKnight ............... A01N 25/00 |
| 2016/0332931 A1* | 11/2016 | Dave ....................... C05G 3/08 |
| 2017/0050895 A1 | 2/2017 | Ortiz-Suarez et al. |
| 2017/0297970 A1 | 10/2017 | McKnight et al. |
| 2018/0162783 A1 | 6/2018 | McKnight et al. |
| 2019/0055169 A1* | 2/2019 | Peters .................... C05G 3/08 |
| 2019/0256437 A1* | 8/2019 | McKnight .............. C05C 9/00 |

FOREIGN PATENT DOCUMENTS

WO 2016054012 A1 4/2016

* cited by examiner

*Primary Examiner* — Wayne A Langel
(74) *Attorney, Agent, or Firm* — Vorys, Sater, Seymour and Pease LLP

(57) ABSTRACT

An inhibitor composition contains alkyl thiophosphoric triamide (or a mixture of alkyl thiophosphoric triamide and dicyandiamide),dissolved in a liquid medium including at least one organic solvent, at least one amine stabilizer and, optionally, at least one dye and/or at least one odor masking agent, is useful in making fertilizer compositions and in a method of fertilizing target plants.

28 Claims, No Drawings

STABILIZED DCD AND/OR ALKYL THIOPHOSPHORIC TRIAMIDE SOLVENT SYSTEMS AND USE IN AGRICULTURAL APPLICATIONS

CROSS-REFERENCE TO RELATED APPLICATIONS

This application is a continuation of U.S. patent application Ser. No. 15/637,110 filed Jun. 29, 2017 which claims the benefit of U.S. Provisional Application Ser. No. 62/356,035, filed Jun. 29, 2016, incorporated herein by reference in its entirety.

FIELD OF THE INVENTION

This invention relates to stabilized liquid compositions comprising dicyandiamide and/or an alkyl thiophosphoric triamide, methods for stabilizing such liquid compositions and the use of such compositions.

BACKGROUND OF THE INVENTION

In the agrochemical industry, farmers use various fertilizers to impart macronutrients to plants either by application to the soil or application to plant leaves. Nitrogen, phosphorus, potassium, calcium, magnesium, and sulfur are macronutrients that must be supplied to the plants and soil manually by farmers. In many crops, the amount of nitrogen supplied is critical to the overall quality and growth of the crop. Nitrogen is typically supplied in the form of nitrogenous, i.e., nitrogen precursor-containing, fertilizer compounds, such as urea, ammonium nitrate, or ammonium phosphate fertilizer compounds. Due to the high water solubility of these salts, however, applied nitrogen values may be lost due to run-off and leaching of the nitrogenous fertilizer compounds. Once applied, the nitrogenous fertilizer compounds are typically degraded, for example, by microorganisms present in the soil, to nitrogenous species such as $NH_4^+$, $NO_2^-$, $NO_3^-$, and ammonia gas, that may be even more readily lost through evaporation, run-off, and leaching than the fertilizer compounds themselves. If degradation of the fertilizer compounds occurs at a rate that is faster than the nitrogenous degradation products can be used by the plants, then the nitrogen values in the degradation products are at increased risk of being lost.

Nitrification and/or urease inhibitors are of potential use in delaying degradation of fertilizer compounds and thereby reducing losses of nitrogenous degradation products that would otherwise occurred in the absence of the inhibitors. The use of nitrification and/or urease inhibitors in combination with nitrogenous fertilizer compounds tends to increase the amount of time the nitrogen sources remain in the soil and available for absorption by the plants, which tends to increase the effectiveness of the fertilizers and positively impact crop yield and quality.

Aqueous end use fertilizer solutions are typically prepared in the field by diluting commercially available concentrated fertilizer compositions with water. Commonly used concentrated fertilizer compositions include concentrated ammonium nitrate compositions, such as, for example, UAN 18, UAN 28, UAN 30 and UAN 32.

Dicyandiamide is potentially useful as a nitrification inhibitor in such aqueous end use fertilizer compositions, but has very low solubility (about 41 grams per liter ("g/l")) in water and so is difficult to be incorporated into the aqueous end use fertilizer compositions, particularly under field conditions.

SUMMARY OF THE INVENTION

Urease inhibitors can be used with a fertilizer (i.e., incorporated into a urea-containing fertilizer, e.g., urea and urea ammonium nitrate (UAN)) to slow the conversion of ammonium to ammonia gas and thus slow the loss of ammonia to volatilization, thus making ammonium available to plants in the soil for longer periods of time. In many crops, the amount of nitrogen supplied is critical to the overall quality and growth of the crop. Nitrogen is supplied in either urea or ammonium phosphate forms. Due to the high water solubility of these salts, however, much of the nitrogen applied is lost to run-off and leaching. In ammonium-based products, if the nitrogen is not lost due to leaching or run-off, it is being converted to ammonia gas by an enzyme called urease where the ammonium ions can bind to soil particles. Conversion occurring near the surface of the soil, however, does not allow for binding and this ammonia is lost to the atmosphere. Urease inhibitors are used to protect a farmer's investment in fertilizers by preventing the breakdown of urea by urease, the soil microbe responsible for converting urea to usable ammonia in the soil. This increases the amount of time the nitrogen remains in the soil and is available to the plant for absorption.

Similarly, nitrification inhibitors can be used with a fertilizer (i.e., incorporated into a urea-containing fertilizer, e.g., urea and urea ammonium nitrate (UAN)) to slow the process of ammonium conversion to nitrate, and subsequently the loss of nitrate to leeching, thus making ammonium available to plants in the soil for longer periods of time. Ammonium is one of the main forms of nitrogen that can be utilized by plants. Increasing the amount of time that the nitrogen is available to the plant increases the effectiveness of the fertilizer which positively impacts crop yield and quality.

Fertilizers, in one embodiment, are common water soluble inorganic fertilizers that provide nutrients such as phosphorus-based, nitrogen-based, potassium-based or sulphur-based fertilizers. Examples of such fertilizers include: for nitrogen as the nutrient: nitrates and or ammonium salts such as ammonium nitrate, including in combination with urea e.g. as Uram type materials, calcium ammonium nitrate, ammonium sulphate nitrate, ammonium phosphates, particularly mono-ammonium phosphate, di-ammonium phosphate and ammonium polyphosphate, ammonium sulphate, and the less commonly used calcium nitrate, sodium nitrate, potassium nitrate and ammonium chloride. It is understood that a fertilizer composition can comprise one or a combination of the fertilizers described herein.

A typical urease inhibitor, alkyl thiophosphoric triamide (for example, N-(n-butyl)-thiophosphoric triamide or otherwise "NBPT"), however, faces drawbacks in its use as NBPT is extremely difficult to handle. NBPT is a sticky, waxy, heat and water sensitive material, which cannot be used in its solid form, as it is used at low concentrations making it difficult to evenly distribute on urea prills (i.e., large granules) and in soil. In order to evenly distribute the NBPT onto the urea, the NBPT should be dispersed into a carrier prior to being sprayed onto the urea. Thus, the use of a solvent system containing the NBPT is desirable as, in its liquid form, the solvent system is capable of distributing the NBPT into granular urea (e.g., urea prills) and into liquid fertilizers containing urea. By introducing the NBPT to liquid fertilizers containing urea (for example, urea-ammonium nitrate solutions or UAN) in a solvent system, the NBPT is capable of being better dispersed in the liquid fertilizer.

Dicyandiamide is useful as a nitrification inhibitor in aqueous agricultural applications, e.g., end use fertilizer compositions, but similar to urease inhibitors face drawbacks. Nitrification inhibitors, such as dicyandiamide, generally have very low solubility (about 41 grams per liter ("g/l")) in water and so it is difficult to incorporate into the aqueous end use fertilizer compositions, particularly under field conditions. As nitrification inhibitors, such as dicyandiamide, have a generally low solubility, they are used at low concentrations in water making it difficult to evenly distribute on urea-containing prills (i.e., large granules) and in soil. In order to evenly distribute the dicyandiamide onto the urea-containing prills or granules, dicyandiamide should be dispersed into a solvent carrier prior to being sprayed onto the urea. Thus, the use of a solvent system containing dicyandiamide (herein, also termed "DCD") is desirable as, in its liquid form, the solvent system is capable of distributing the dicyandiamide onto urea granules or prills, urea ammonium nitrate granules or prills or, otherwise, urea-containing granules or prills, and into liquid fertilizers containing urea or urea ammonium nitrate. By introducing the dicyandiamide to liquid fertilizers containing urea (for example, urea-ammonium nitrate solutions or UAN) in a solvent system, the dicyandiamide is capable of being better dispersed in the liquid fertilizer.

In one embodiment, concentrated fertilizer compositions include concentrated ammonium nitrate compositions, such as, for example, UAN 18, UAN 28, UAN 30 and UAN 32.

Thus, in one embodiment, it is desirable to have a solvent system containing alkyl thiophosphoric triamide, for example, (N-(n-butyl)-thiophosphoric triamide), that has a favorable toxicological and/or ecological profile and desirable characteristics in terms of low volatility, biodegradability or ready biodegradability (i.e., readily biodegradable), low toxicity or low hazard level. In another embodiment, it is desirable to have a solvent system containing a nitrification inhibitor, for example, dicyandiamide, that has a favorable toxicological and/or ecological profile and desirable characteristics in terms of low volatility, biodegradability or ready biodegradability (i.e., readily biodegradable), low toxicity or low hazard level. In a further embodiment, it is desirable to have a solvent system containing a combination of a nitrification inhibitor and urease inhibitor that has a favorable toxicological and/or ecological profile and desirable characteristics in terms of low volatility, biodegradability or ready biodegradability (i.e., readily biodegradable), low toxicity or low hazard level.

Another problem is that certain nitrification inhibitors and/or urease inhibitors degrade at varying temperatures and extreme conditions, e.g., high temperatures or low temperatures. For example, NBPT—a urease inhibitor—degrades rapidly at higher temperature, typically, above 45° C. Often times temperatures in agricultural fields (e.g., corn fields, wheat fields, etc.) reach in excess of 35° C. and sometimes can reach up to 45° C. or higher. For example, at 45° C. NBPT formulated in different solvents changes color in days from colorless to a darker green/brown, followed by sludge/precipitate formation after weeks had been exposed to high heat. Thus, it is also desirable to have solvent systems containing nitrification inhibitors and/or urease inhibitors that are stable at high temperatures, such as those utilized in hot climates or weather. This invention addresses the addition of stabilizers to prolong the chemical and physical stability of formulated liquid agricultural compositions containing (i) one or more nitrification inhibitors, (ii) one or more urease inhibitors or (iii) a combination of both (i) and (ii). In one embodiment, the urease inhibitor is NBPT. In one embodiment, the nitrification inhibitor is DCD.

There is also a need for improved NBPT formulations in DMSO to reduce decomposition of N-(n-butyl) thiophosphoric triamide (NBPT) into non-effective substances. This decomposition can be observed through common signs of degradation while undergoing long-term storage stability studies. Specifically other side-products suspected of reacting with DMSO in formulation leaving large amounts of sediment and/or malodor in the formulation generated while undergoing stability studies. The above mentioned disadvantages can be solved by adding a co-solvent to reduce NBPT degradation during a long-term storage resulting in unwanted sedimentation and/or odor masking agent to minimize any malodor in the formulation.

The present invention described herein will become apparent from the following detailed description and examples, which comprises in one aspect, a liquid composition for use in agricultural applications comprising: at least one of a nitrification inhibitor or a urease inhibitor; at least one solvent; and at least one stabilizer. In one particular embodiment, the at least one stabilizer is an amine stabilizer. In one embodiment, the liquid composition further comprises a dye.

In one embodiment, the amine stabilizer is an alkanolamine. In another embodiment, the amine stabilizer is a monoalkanolamine. In another embodiment, the amine stabilizer is a dialkanolamine. In another embodiment, the amine stabilizer is a trialkanolamine. In yet another embodiment, the amine stabilizer is a monoethanolamine. In a further embodiment, the amine stabilizer is a diethanolamine. In yet a further embodiment, the amine stabilizer is a triethanolamine. In another embodiment, the alkanol group is chosen from methanol, ethanol, propanol, butanol. In one embodiment, the amine stabilizer is selected from 2-amino-2-methyl-1-propanol, Amino-2-propanol, 2-Amino-1-butanol or any combination thereof.

In one embodiment, the amine stabilizer is 2-amino-2-methyl-1-propanol. In one embodiment, the amine stabilizer is Amino-2-propanol. In one embodiment, the amine stabilizer is 2-Amino-1-butanol.

In another aspect, described herein are methods of making a solid or concentrated liquid fertilizer compositions comprising treating (e.g., contacting or spray applying) one or more nitrogenous fertilizer compounds with a liquid inhibitor composition. The liquid inhibitor composition comprises a nitrification inhibitor and/or a urease inhibitor, homogenously dissolved or dispersed in a solvent comprising at least one amine stabilizer as described above. The liquid inhibitor composition, in one embodiment, further comprises at least one organic co-solvent selected from polar aprotic solvents, amine solvents, heterocyclic alcohol solvents, and mixtures thereof.

The term treating, in one embodiment, includes spray applying the liquid inhibitor composition with the one or more nitrogenous fertilizer compounds. The term treating, in one embodiment, includes but is not limited to contacting the inhibitor composition with the one or more nitrogenous fertilizer compounds. In one embodiment, the nitrification inhibitor is dicyandiamide (otherwise referred to herein as "DCD"). In another embodiment, the urease inhibitor is an alkyl thiophosphoric triamide.

In yet another aspect, described herein are concentrated liquid fertilizer compositions comprising, based on weight of the composition: (a) up to about 99 wt %, by weight of composition, of one or more nitrogenous fertilizer compounds, (b) at least one alkyl thiophosphoric triamide or an alkyl thiophosphoric triamide in combination with dicyandiamide, (c) at least one solvent as described herein and (d) at least one amine stabilizer.

In a further aspect, described herein are concentrated liquid fertilizer compositions comprising, based on weight of the composition: (a) up to about 99 wt %, by weight of composition, of one or more nitrogenous fertilizer compounds, (b) at least one of a dicyandiamide and/or an alkyl thiophosphoric triamide, (c) optionally, at least one organophosphate compound according to formula (I.a), (d) at least one solvent selected from polar aprotic solvents, heterocyclic alcohol solvents, and mixtures thereof, (e) at least one amine stabilizer and (f) optionally, water. The concentrated liquid fertilizer compositions can further comprise one or more stabilizers.

In yet another aspect, described herein are solid or substantially solid fertilizer compositions comprising: (a) solid particles of one or more nitrogenous fertilizer compounds, and (b) an inhibitor composition comprising at least one of a dicyandiamide or an alkyl thiophosphoric triamide supported on at least a portion of the solid particles. In one embodiment, the inhibitor composition covers substantially all of the solid particles. In one embodiment, evenly covers (or substantially evenly covers) all of the solid particles.

In another aspect, described herein are methods of making stable liquid or aqueous fertilizer composition comprising contacting one or more nitrogenous fertilizer compounds, with a liquid inhibitor composition that comprises at least one of a nitrification inhibitor or a urease inhibitor, homogenously dissolved or dispersed in a solvent comprising at least one amine stabilizer. In one embodiment, the amine stabilizer is 2-amino-2-methyl-1-propanol. In one embodiment, the amine stabilizer is Amino-2-propanol. In one embodiment, the amine stabilizer is 2-Amino-1-butanol. In one embodiment, the amine stabilizer is monoethanolamine. The solvent can, optionally, further comprise an organic co-solvent selected from polar aprotic solvents, amine solvents, heterocyclic alcohol solvents, and mixtures thereof.

In another aspect, the organophosphate compound has the formula (I.a)

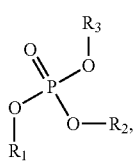

(I.a)

wherein $R_1$, $R_2$ and $R_3$, are each independently chosen from H, a $C_1$-$C_{16}$ alkyl group, a $C_1$-$C_{16}$ alkenyl, group, a $C_1$-$C_{16}$ alkoxyalkyl group, a $C_7$-$C_{30}$ alkylarylalkyl group, a $C_7$-$C_{30}$ arylalkyl group, or an aryl group; provided that at least one of $R_1$, $R_2$ or $R_3$ is not H. In another embodiment, $R_1$, $R_2$ and $R_3$, are each independently chosen from H, a $C_1$-$C_{12}$ alkyl group, a $C_1$-$C_{12}$ alkenyl, group, a $C_1$-$C_{12}$ alkoxyalkyl group, a $C_7$-$C_{30}$ alkylarylalkyl group, a $C_7$-$C_{30}$ arylalkyl group, or an aryl group; provided that at least one of $R_1$, $R_2$ or $R_3$ is not H. In one embodiment, $R_1$, $R_2$ and $R_3$, are each independently chosen from H, a $C_1$-$C_4$ alkyl group, a $C_4$-$C_8$ alkyl group, a $C_1$-$C_{12}$ alkenyl, group, a $C_1$-$C_4$ alkoxyalkyl group, a $C_7$-$C_{30}$ alkylarylalkyl group, a $C_7$-$C_{30}$ arylalkyl group, or an aryl group; provided that at least one of $R_1$, $R_2$ or $R_3$ is not H.

In yet another embodiment, $R_1$, $R_2$ and $R_3$, are each independently chosen from a $C_1$-$C_{12}$ alkyl group, a $C_1$-$C_{12}$ alkenyl, group, a $C_1$-$C_{12}$ alkoxyalkyl group, a $C_7$-$C_{30}$ alkylarylalkyl group, a $C_7$-$C_{30}$ arylalkyl group, or an aryl group. In one embodiment, $R_1$, $R_2$ and $R_3$, are each independently chosen from a $C_1$-$C_{12}$ alkyl group, more typically, a $C_2$-$C_8$ alkyl group.

In another aspect, described herein are methods for fertilizing target plants, comprising applying an aqueous end use fertilizer composition that comprises: (a) one or more nitrogenous fertilizer compounds, (b) at least one of a dicyandiamide or an alkyl thiophosphoric triamide, typically, alkyl thiophosphoric triamide, (c) at least one solvent comprising dimethyl sulfoxide, dimethyl formamide, monoethanolamine, amino-2-propanol, dimethylaminoethanol, triethanol amine, a heterocyclic alcohol according to formula (II.a):

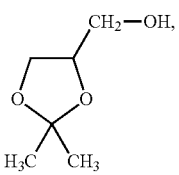

(II.a)

or mixtures thereof, (d) an amine stabilizer, and optionally, (e) water, to the target plants or to an environment for the target plants. It is understood that the term heterocyclic alcohol includes dioxolane compounds. The end use fertilizer composition can also comprise, in some embodiments, at least one stabilizer other than an amine stabilizer, which in one embodiment is an organophosphate compound.

In one embodiment, the alkyl thiophosphoric triamide is N-(n-butyl)-thiophosphoric triamide. In another embodiment, the liquid composition comprises dimethyl sulfoxide and at least one co-solvent selected from the group consisting of: (a) at least one dioxolane compound of formula (II.b):

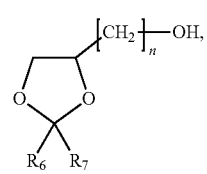

(II.b)

wherein $R_6$ and $R_7$ individually comprises a hydrogen, an alkyl group, an alkenyl group, or a phenyl group, wherein n is an integer of from 1 to 10; b) at least one dibasic ester; c) at least one compound of formula (III):

R₃OOC-A-CONR₄R₅    (III), wherein R3 comprises a C1-C36 alkyl group; wherein R4 and R5 individually comprise a C1-C36 alkyl group, wherein R4 and R5 can optionally together form a ring; and wherein A is a linear or a branched divalent C2-C12 alkyl group; d) at least one alkanolamine or alkoxylated alkanolamine; e) at least one glycol or glycol derivative; f) at least one organophosphate compound and g) any combination thereof.

In another aspect, the present invention is directed to a nitrification inhibitor composition comprising dicyandiamide dissolved in a liquid medium that comprises an organic solvent selected from polar aprotic solvents, dibasic esters, amines, amino alcohols, heterocyclic alcohols, and mixtures thereof.

In yet another aspect, the present invention is directed to a method of making a solid or concentrated liquid fertilizer composition comprising treating (e.g., contacting, spray applying, brushing, etc.) one or more nitrogenous fertilizer compounds with a nitrification inhibitor composition that comprises dicyandiamide dissolved in a liquid medium that comprises an organic solvent selected from polar aprotic solvents, amine solvents, heterocyclic alcohol solvents, and mixtures thereof.

In a further aspect, the present invention is directed to a concentrated liquid fertilizer composition comprising, by weight of the composition:
(a) up to about 99 wt % of one or more nitrogenous fertilizer compounds,
(b) an alkyl thiophosphoric triamide or dicyandiamide (or a combination thereof);
(c) at least one amine stabilizer;
(d) at least one solvent selected from polar aprotic solvents, amine solvents, heterocyclic alcohol solvents, or mixtures thereof, and
(d) optionally, water.

In another aspect, the present invention is directed to a concentrated solid fertilizer composition comprising:
(a) solid particles of one or more nitrogenous fertilizer compounds, and
(b) dicyandiamide or an alkyl thiophosphoric triamide supported on at least a portion of the solid particles.

In one embodiment, the carrier utilized to contact the dicyandiamide or an alkyl thiophosphoric triamide with the solid particles comprises at least one solvent as described herein and an amine stabilizer as described herein.

In yet another aspect, the present invention is directed to a method of making a stable, aqueous end use fertilizer composition comprising contacting one or more nitrogenous fertilizer compounds with a urease inhibitor composition that comprises an alkyl thiophosphoric triamide dissolved in a liquid medium that comprises an organic solvent selected from polar aprotic solvents, amine solvents, heterocyclic alcohol solvents, or mixtures thereof, in addition to an amine stabilizer.

In a further aspect, the present invention is directed to a method for fertilizing target plants, comprising applying an aqueous end use fertilizer composition that comprises:
(a) one or more nitrogenous fertilizer compounds;
(b) dicyandiamide, an alkyl thiophosphoric triamide, or a mixture thereof;
(c) an amine stabilizer,
(d) at least one organic solvent;
(e) optionally, at least one dye, and
(f) optionally, water,
to the target plants or to an environment for the target plants.

DETAILED DESCRIPTION

As used herein, the term "alkyl" means a saturated straight chain, branched chain, or cyclic hydrocarbon radical, including but not limited to, methyl, ethyl, n-propyl, iso-propyl, n-butyl, sec-butyl, t-butyl, pentyl, n-hexyl, and cyclohexyl.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkenyl, halo, haloalkyl, or amino, including but not limited to, phenoxy, phenyl, methylphenyl, dimethylphenyl, trimethylphenyl, chlorophenyl, trichloromethylphenyl, aminophenyl, and tristyrylphenyl.

As used herein, the term "alkylene" means a divalent saturated straight or branched chain hydrocarbon radical, such as for example, methylene, dimethylene, trimethylene.

As used herein, the term "alkoxyl" means an oxy radical that is substituted with an alkyl group, such as for example, methoxyl, ethoxyl, propoxyl, isopropoxyl, or butoxyl, which may optionally be further substituted on one or more of the carbon atoms of the radical.

As used herein, the term "alkoxyalkyl" means an alkyl radical that is substituted with one or more alkoxy substituents, more typically a $(C_1$-$C_{22})$alkyloxy-$(C_1$-$C_6)$alkyl radical, such as methoxymethyl, and ethoxybutyl.

As used herein, the term "alkenyl" means an unsaturated straight or branched hydrocarbon radical, more typically an unsaturated straight, branched, (which, in one particular embodiment, is $C_1$-$C_{75}$) hydrocarbon radical, that contains one or more carbon-carbon double bonds, such as, for example, ethenyl, n-propenyl, iso-propenyl.

As used herein, the term "arylalkyl" means an alkyl group substituted with one or more aryl groups, more typically a $(C_1$-$C_{18})$alkyl substituted with one or more $(C_6$-$C_{14})$aryl substituents, such as, for example, phenylmethyl, phenylethyl, and triphenylmethyl.

As used herein, the term "aryloxy" means an oxy radical substituted with an aryl group, such as for example, phenyloxy, methylphenyl oxy, isopropylmethylphenyloxy.

As used herein, the terminology "$(C_r$-$C_s)$" in reference to an organic group, wherein r and s are each integers, indicates that the group may contain from r carbon atoms to s carbon atoms per group.

In one embodiment, non-limiting examples of nitrification inhibitors comprise any one or more of N-2,5-dichlorophenyl succinamic acid, dicyandiamide (DCD), zinc ethylene-bis-dithiocarbamate, 2,4,6-triehloroaniline, pentachlorophenol, thio-urea, ammonium thiosulphate (ATS) or 3,4-dimethypyrazole phosphate (DMPP).

In one embodiment, non-limiting examples of urease inhibitors comprise any one or more of N-butyl thiophosphoric triamide (NBPT), N-(w-butyl)phosphoric triamide, miophosphoryl triamide, cyclohexyl phosphoric triamide, cyclohexyl thiophosphoric triamide, phosphoric triamide, hydroquinone, p-benzoquinone, hexamidocyclotriphosphazene, thiopyridines, thiopyrimidines, thiopyridine-N-oxides, N,A'-dihalo-2-imidazolidinone, N-halo-2-oxazolidinone, ammonium thiosulphate (ATS), N-cyclohexyl phosphoric triamide (CHPT), phenyl phosphorodiamidate (PPT) and 2-nitrophenyl phosphoric triamide (2-NPT).

Dicyandiamide is a known compound according to formula (I.b):

(I.b)

$$N\equiv C-\underset{H}{N}-\underset{NH_2}{\overset{NH}{C}}.$$

Dicyandiamide, also known as "2-cyanoguanidine", is typically made by treating cyanamide with base and is commercially available.

In one embodiment, the compositions according to the present invention comprise a urease inhibitor, such as an alkyl thiophosphoric triamide or ammonium thiosulfate, a nitrification inhibitor, or a combination of both a urease inhibitor and a nitrification inhibitor.

In one embodiment, alkyl thiophosphoric triamide is N-(n-butyl)-thiophosphoric triamide ("NBPT"). The at least one of alkyl thiophosphoric triamide or dicyandiamide or combination thereof can be present in the liquid agricultural composition at a lower range of 2% by weight of the composition. In another embodiment, the at least one of alkyl thiophosphoric triamide or dicyandiamide or combination thereof can be present in the liquid agricultural composition at a lower range of 3% by weight of the composition. The at least one of alkyl thiophosphoric triamide or dicyandiamide or combination thereof can be present in the liquid agricultural composition at a lower range of 5% by weight of the composition.

In another embodiment, at least one of urease inhibitor and/or nitrification inhibitor can be present in the liquid agricultural composition at a lower range of 0.5%, or 1%, or 2%, or 3%, or 4%, or 5%, 6%, or 8%, or 10% or 12% or 14%, by weight of the composition. In another embodiment, at least one of alkyl thiophosphoric triamide and/or dicyandiamide can be present in the liquid agricultural composition at a lower range of 0.5%, or 1%, or 2%, or 3%, or 4%, or 5%, 6%, or 8%, or 10% or 12% or 14%, by weight of the composition.

In another embodiment, the at least one urease inhibitor or nitrification inhibitor or combination thereof can be present in the liquid agricultural composition at an upper range of 75%, or 65%, or 60% by weight of the composition. In another embodiment, the at least one of alkyl thiophosphoric triamide or dicyandiamide or combination thereof can be present in the liquid agricultural composition at an upper range of 75%, or 65%, or 60% by weight of the composition. In another embodiment, the at least one of alkyl thiophosphoric triamide or dicyandiamide or combination thereof can be present in the liquid agricultural composition at an upper range of 60% by weight of the composition. In another embodiment, the at least one of alkyl thiophosphoric triamide or dicyandiamide or combination thereof can be present in the liquid agricultural composition at an upper range of 55% by weight of the composition.

In another embodiment, the at least one urease inhibitor or nitrification inhibitor or combination thereof can be present in the liquid agricultural composition at an upper range of 59%, or 57%, or 55% or 53% or 50%, by weight of the composition. In another embodiment, at least one of alkyl thiophosphoric triamide and/or dicyandiamide can be present in the liquid agricultural composition at an upper range of 59%, or 57%, or 55% or 53% or 50%, by weight of the composition.

In another embodiment, the at least one urease inhibitor or nitrification inhibitor or combination thereof can be present in the liquid agricultural composition at an upper range of 48%, or 46%, or 45% or 42% or 40%, by weight of the composition. In another embodiment, at least one of alkyl thiophosphoric triamide and/or dicyandiamide can be present in the liquid agricultural composition at an upper range of 48%, or 46%, or 45% or 42% or 40%, by weight of the composition.

In another embodiment, the at least one of alkyl thiophosphoric triamide or dicyandiamide or combination thereof can be present in the liquid agricultural composition at an upper range of 35% by weight of the composition. In another embodiment, the at least one of alkyl thiophosphoric triamide or dicyandiamide or combination thereof can be present in the liquid agricultural composition at an upper range of 30% by weight of the composition. In another embodiment, the at least one of alkyl thiophosphoric triamide or dicyandiamide or combination thereof can be present in the liquid agricultural composition at an upper range of 25% by weight of the composition.

In another embodiment, the at least one of alkyl thiophosphoric triamide or dicyandiamide can be present in the liquid agricultural composition in an amount between about 7% by weight of the composition to about 55% by weight of the composition. In another embodiment, the at least one of alkyl thiophosphoric triamide or dicyandiamide can be present in the composition in an amount between about 8% by weight of the composition to about 50% by weight of the composition. In another embodiment, the at least one of alkyl thiophosphoric triamide or dicyandiamide can be present in the liquid agricultural composition in an amount between about 7% by weight of the composition to about 45% by weight of the composition. In another embodiment, the at least one of alkyl thiophosphoric triamide or dicyandiamide can be present in the liquid agricultural composition in an amount between about 7% by weight of the composition to about 40% by weight of the composition. In another embodiment, the at least one of alkyl thiophosphoric triamide or dicyandiamide can be present in the liquid agricultural composition in an amount between about 7% by weight of the composition to about 35% by weight of the composition.

The at least one of alkyl thiophosphoric triamide or dicyandiamide can be present in the composition in an amount between about 0.5% by weight of the composition and about 60% by weight of the composition or, in another embodiment, can be present in the composition in an amount between about 1% by weight of the composition and about 40% by weight of the composition, and, in another embodiment, can be present in the composition in an amount between about 0.5% by weight of the composition and about 20% by weight of the composition. In one particular embodiment, the at least one of alkyl thiophosphoric triamide or dicyandiamide is present in the composition in an amount between about 1% by weight of the composition and about 30% by weight of the composition. The at least one of alkyl thiophosphoric triamide or dicyandiamide means that alkyl thiophosphoric triamide can be solely present, dicyandiamide can be solely present, or a combination of alkyl thiophosphoric triamide and dicyandiamide is present.

The stabilizer can be any suitable amine compound. Compounds suitable as the at least one amine stabilizer include alkanolamines and alkoxylated alkanolamines. In one embodiment, the amine stabilizer is 2-amino-2-methyl-1-propanol (sometimes referred to as "AMP"). In one embodiment, the amine stabilizer is Amino-2-propanol. In one embodiment, the amine stabilizer is 2-Amino-1-butanol. In one embodiment, the amine stabilizer is a monoalkanolamine. In another embodiment, the amine stabilizer is a dialkanolamine. In another embodiment, the amine stabilizer is a trialkanolamine. In yet another embodiment, the amine stabilizer is a monoethanolamine. In a further embodiment, the amine stabilizer is a diethanolamine. In yet a further embodiment, the amine stabilizer is a triethanolamine. In another embodiment, the alkanol group is chosen from methanol, ethanol, propanol, butanol. In one embodiment, the alkoxylate alkanolamine is an aminoalkoxy alcohol.

In one embodiment, the amine stabilizer is according to formula (IV):

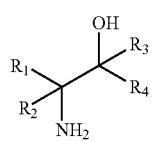

(IV)

wherein $R_1$ is H, $CH_3$, $CH_2CH_3$, or a branched or linear $C_2$-$C_5$ alkyl group, $R_2$ is H, $CH_3$, $CH_2CH_3$, or a branched or linear $C_2$-$C_5$ alkyl group, $R_3$ is H, $CH_3$ or a branched or linear $C_2$-$C_5$ alkyl group, and $R_4$ is H, $CH_3$ or a branched or linear $C_2$-$C_5$ alkyl group. In one embodiment, $R_1$ is $CH_3$, $R_2$ is $CH_3$, $R_3$ is H, and $R_4$ is H. In another embodiment, $R_1$ is H, $R_2$ is H, $R_3$ is $CH_3$, and $R_4$ is H. In yet another embodiment, $R_1$ is $CH_2CH_3$, $R_2$ is H, $R_3$ is H, and $R_4$ is H.

In one embodiment, the amine stabilizer is 1,2-diaminocyclohexane (DCH) or Bis(hexamethylene)triamine (BHT). In another embodiment the amine stabilizer is selected from monoethanolamine, ethylaminoethanol, dimethylaminoethanol, isopropylaminoethanol, diethanolamine, triethanolamine, methylaminoethanol, aminopropanol, methylaminopropanol, dimethylaminopropanol, aminobutanol, dimethylaminobutanol, aminobutanediol, trihydroxymethylaminoethane, diethylaminopropanediol, 1-amino-cyclopentane methanol, and aminobenzyl alcohol, or a heterocyclic ring that comprises at least one nitrogen atom as a ring member and/or is substituted on at least one carbon atom with an amino group and that is substituted on at least one other carbon atom with a hydroxyalkyl or hydroxyl group, such as methylaminomethyl-1,3-dioxolane.

The amine stabilizer component can form stable compositions when combined with solvent compositions containing the nitrification and/or urease inhibitor, which in some embodiments means stability at temperatures ranging from −16° C. to 54° C., in other embodiments, −10° C. to 40° C., in other embodiments, −5° C. to 40° C., in other embodiments, −2° C. to 40° C., or in other embodiments, 0° C. to 40° C.

In one embodiment, the stabilizer or amine stabilizer is present in the liquid composition in an amount between about 0.5% by weight of the composition to about 15% by weight of the composition. (It is understood that the term "%" can be used interchangeably with "wt %")

In one embodiment, the stabilizer or amine stabilizer is present in the liquid composition at a lower range of 0.1%, or 0.2%, or 0.3%, or 0.4%, or 0.5%, or 0.6%, or 0.8%, or 1% or 1.2% or 1.4%, by weight of the composition. In one embodiment, the stabilizer or amine stabilizer is present in the liquid composition at a lower range of 1%, or 2%, or 3%, or 4%, or 5%, or 6%, or 7%, or 8%, or 10% by weight of the composition.

In one embodiment, the stabilizer or amine stabilizer is present in the liquid composition at an upper range of 10%, or 11%, or 12%, or 13%, or 14%, or 15% by weight of the composition. In one embodiment, the stabilizer or amine stabilizer is present in the liquid composition at an upper range of 16%, or 18%, or 20%, or 22%, or 24%, or 26%, or 28%, or 30% by weight of the composition.

In another embodiment, compounds suitable as the organic solvent are polar aprotic solvents, heterocyclic alcohol solvents, and/or mixtures thereof, that form liquid, or otherwise stable, compositions with the nitrification and/or urease inhibitor at temperatures at or greater than −16° C., in alternative embodiments, greater than −14° C., in other embodiments, greater than −12° C., in other embodiments, greater than −10° C., in further embodiments, greater than −8° C., in other embodiments, greater than −5° C., in other embodiments, greater than −3° C., in other embodiments, greater than −2° C., in other embodiments, greater than 0° C., in other embodiments, greater than 2° C., in other embodiments, greater than 4° C., in other embodiments, greater than 5° C.

In some embodiments, at high temperature ranges or at greater than a specified temperature (as described herein), the liquid fertilizer composition is stable, meaning the urease and/or nitrification inhibitor(s) do not react with the solvent or solvent component under anticipated manufacturing, storage, and use conditions. In one embodiment, the liquid fertilizer compositions are stable at a temperature greater than 25° C. In one embodiment, the liquid fertilizer compositions are stable at a temperature greater than 27° C. In one embodiment, the liquid fertilizer compositions are stable at a temperature greater than 29° C. In one embodiment, the liquid fertilizer compositions are stable at a temperature greater than 30° C. In one embodiment, the liquid fertilizer compositions are stable at a temperature greater than 32° C. In one embodiment, the liquid fertilizer compositions are stable at a temperature greater than 34° C. In one embodiment, the liquid fertilizer compositions are stable at a temperature greater than 35° C. In one embodiment, the liquid fertilizer compositions are stable at a temperature greater than 37° C. In one embodiment, the liquid fertilizer compositions are stable at a temperature greater than 40° C. In one embodiment, the liquid fertilizer compositions are stable at a temperature greater than 42° C. In one embodiment, the liquid fertilizer compositions are stable at a temperature greater than 44° C. In one embodiment, the liquid fertilizer compositions are stable at a temperature greater than 45° C. In one embodiment, the liquid fertilizer compositions are stable at a temperature greater than 47° C. In one embodiment, the liquid fertilizer compositions are stable at a temperature greater than 50° C.

In one embodiment, at the specified temperature ranges or at greater than a specified temperature (as described herein), the liquid fertilizer composition is stable, meaning the liquid fertilizer composition is or substantially is in one phase, i.e., no visible crystals, no visible precipitation, and/or no visible multiple liquid phases. In another embodiment, the liquid fertilizer composition is stable, meaning the liquid fertilizer composition is or substantially is in one phase and shows little or slight discoloration.

In one embodiment, the liquid fertilizer composition is stable, meaning that the co-solvent does not degrade or chemically react to other components in the composition.

In one embodiment, the liquid fertilizer compositions contains an organophosphate compound according to formula (I.a) (wherein $R_1$, $R_2$ and $R_3$ are as described above).

Suitable polar aprotic organic solvents include, for example, dichloromethane, dimethyl acetamide, dimethyl formamide, dimethyl sulfoxide, ethyl acetate, hexamethylphosphoramide, dimethyl sulfone, sulfolane, 1,3-dimethyl-2-imidazoidinone, 1,3-dimethyl-3,4,5,6-tetrahydro-2(1H)-pyrimidone, methyl acetate, ethyl lactate, methylpyrrolidone, tetrahydrofuran, propylene carbonate, and dibasic ester solvents.

Suitable dibasic ester solvents include, for example, dialkyl esters of dicarboxylic acids, more typically, the di($C_1$-$C_{12}$)alkyl esters of saturated linear or branched ($C_2$-$C_8$)aliphatic carboxylic acids or a mixture thereof. In one embodiment, the dibasic ester component comprises one or more compounds according to formula (III):

wherein:
A is a divalent linear or branched ($C_2$-$C_8$)aliphatic group, and
$R^1$, $R^2$, and $R^3$ are each independently ($C_1$-$C_{12}$)alkyl, ($C_1$-$C_{12}$)aryl, ($C_1$-$C_{12}$)alkaryl or ($C_1$-$C_{12}$)arylalkyl, and $R^2$ and $R^3$ may each optionally be substituted with one or more hydroxyl groups.

Glycols and glycol derivatives include but are not limited to aliphatic dihydroxy (dihydric) alcohols. In one embodiment, glycol derivatives include but are not limited to polypropylene glycol, triethylene glycol, glycol alkyl ethers such as dipropylene glycol methyl ether, diethylene glycol. In another embodiment, glycol derivatives include but are not limited to polyglycols such as polyethylene glycols (PEG) and polypropylene glycols. Glycols are represented by the general formula $C_nH_{2n}(OH)_2$, where n is at least 2. Non-limiting examples of glycols include ethylene glycol (glycol), propylene glycol (1,2-propanediol), 1,4-butanediol, 1,5-pentanediol, 1,6-hexanediol, 1,7-heptanediol, 1,9-nonanediol, 1,10-decanediol, 1,8-octanediol, 1,3-propanediol, 1,3-butanediol, 1,4-butanediol, 2,3-butanediol, 2,4-pentanediol, 2,5-hexanediol, 4,5-octanediol and 3,4-hexanediol, neopenty glycol, pinacol, 2,2-diethyl-1,3-propanediol, 2-ethyl-1,3-hexanediol, 2-ethyl-2-butyl-1,3-propanediol, isobutylene glycol, 2,3-dimethyl-1,3-propanediol, 1,3-diphenyl-1,3-propanediol, 3-methyl-1,3-butanediol.

In another embodiment, glycol derivatives include but are not limited to glycol stearate, ethylene glycol monostearate, ethylene glycol distearate, ethylene glycol amido stearate, dilaurate glycol, propylene glycol monostearate, propylene glycol dicaprylate, propylene glycol dicaprate diacetate glycol, dipalmite glycol, diformate glycol, dibutyrate glycol, dibenzorate glycol, dipalmate glycol, dipropionate glycol, monoacetate glycol, monopalmitate glycol and monoformate glycol. In another embodiment, glycol derivatives also include polypropylene glycol, triethylene glycol, dipropylene glycol methyl ether, or diethylene glycol.

Polyglycol derivatives include but are not limited to polyethylene glycol (PEG) 200-6000 mono and dilaurates, such as, PEG 600 dilaurate, PEG 600 monolaurate, PEG 1000 dilaurate, PEG 1000 monolaurate, PEG 1540 dilaurate and PEG 1540 monolaurate, polyethylene glycol 200-6000 mono and dioleates, such as, PEG 400 monoleate, PEG 600 dioleate, PEG 600 monooleate, PEG 1000 monoleate, PEG 1540 dioleate, PEG 1540 monooleate and polyethylene glycol 200-6000 mono and distearates, such as, PEG 400 distearate, PEG 400 monostearate, PEG 600 distearate, PEG 600 monostearate, PEG 1000 distearate, PEG 1000 monostearate, PEG 1540 distearate, PEG 1540 monostearate and PEG 3000 monostearate.

Examples of glycerol derivatives include but are not limited to glycerol monolaurate, glycerol monostearate, glycerol distearate, glycerol trioleate, glycerol monooleate, glycerol dilaurate, glycerol dipalmitate, glycerol triacetate, glycerol tribenzoate, glycerol tributyrate, glycerol monopalmitate, glycerol trimyristate, glycerol trilaurate, glycerol tripalmitate and glycerol tristearate.

Suitable heterocyclic alcohol solvents include, for example, 5- or 6-membered heterocyclic rings that include 1 or 2 oxygen atoms as ring member, that are substituted on at least one carbon atom of the ring with a ($C_1$-$C_6$)hydroxyalkyl group, and that may optionally be substituted on one or more carbon atoms of the ring with one or more ($C_1$-$C_4$) alkyl groups. It is understood that the term heterocyclic alcohol includes dioxolane compounds. In one embodiment, the heterocyclic alcohol component of the present invention comprises a one or more compounds selected from heterocyclic alcohols according to formulas (II.c), (II.d), (II.e), (II.f), and (II.g):

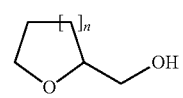
(II.c)

wherein n=1 or 2,

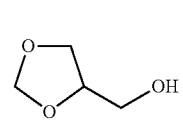
(II.d)

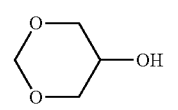
(II.e)

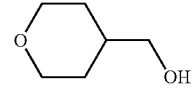
(II.f)

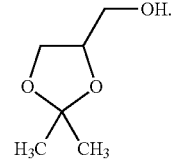
(II.g)

In one embodiment, the organic solvent component comprises one or more dibasic ester compounds, one or more amino alcohols, one or more tertiary amines, one or more heterocyclic alcohols according to formulas (II.a-II.g), or mixtures thereof.

In one embodiment, the organic solvent component of the composition and methods of the present invention comprises dimethyl sulfoxide, monoethanolamine, methyl-5-(dimethylamino)-2-methyl-oxopentanoate, dimethylaminoethanol, triethanol amine, a heterocyclic alcohol according to any of formulas (II.a-II.g), or a mixture thereof.

In one embodiment, the organic solvent component of the composition and methods of the present invention comprises a mixture of at least one organophosphate solvent according to formula (I.a), wherein $R_1$, $R_2$ and $R_3$ are as described above.

In one embodiment, a compound utilized as the solvent or as a component in the solvent blend is a compound of general formula (III):

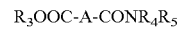

According to one embodiment, the expression "compound" denotes any compound corresponding to the general formula (III). In other embodiments, the term "compound" also refers to mixtures of several molecules corresponding to general formula (III). It may therefore be a molecule of formula (III) or a mixture of several molecules of formula (III), wherein both fall under the definition of the term "compound" when referring to formula (III).

The $R_3$, $R_4$ and $R_5$ groups can be, in some embodiments, identical or, in other embodiment, different. In one embodiment, may be groups chosen from $C_1$-$C_{20}$ alkyl, aryl, alkaryl or arylalkyl groups or the phenyl group. In another embodiment, may be groups chosen from $C_1$-$C_{12}$ alkyl, aryl, alkaryl or arylalkyl groups or the phenyl group. Mention is made especially of Rhodiasolv® PolarClean (Manufactured by Solvay USA Inc., Princeton, N.J.). The $R_4$ and $R_5$ groups may optionally be substituted. In one particular embodiment, the groups are substituted with hydroxyl groups.

In one embodiment, $R_3$ group is chosen from methyl, ethyl, propyl, isopropyl, n-butyl, isobutyl, n-pentyl, isopentyl, isoamyl, n-hexyl, cyclohexyl, 2-ethylbutyl, n-octyl, isooctyl, 2-ethylhexyl, tridecyl groups.

$R_4$ and $R_5$ groups, which are identical or different, in one embodiment, may especially be chosen from methyl, ethyl, propyl (n-propyl), isopropyl, n-butyl, isobutyl, n-pentyl, amyl, isoamyl, hexyl, cyclohexyl or hydroxyethyl groups. The $R_4$ and $R_5$ groups may also be such that they form, together with the nitrogen atom, a morpholine, piperazine or piperidine group. According to some embodiments, $R_4$ and $R_5$ are each methyl, or $R_4$ and $R_5$ are each ethyl, or $R_4$ and $R_5$ are each hydroxyethyl.

According to one embodiment, if A comprises a linear group of formula —$CH_2$—$CH_2$— and/or of formula —$CH_2$—$CH_2$—$CH_2$—$CH_2$— and/or of formula —$(CH_2)_8$— then it is a mixture of A groups. According to one particular embodiment, if A is linear, then it is a mixture of A groups, for example a mixture of two or three —$CH_2$—$CH_2$— (ethylene); —$CH_2$—$CH_2$—$CH_2$— (n-propylene); and —$CH_2$—$CH_2$—$CH_2$—$CH_2$— (n-butylene) groups (or isomers thereof).

According to a first particular embodiment of the invention, the A group is a divalent linear alkyl group chosen from the groups of the following formulae: —$CH_2$—$CH_2$— (ethylene); —$CH_2$—$CH_2$—$CH_2$— (n-propylene); —$CH_2$—$CH_2$—$CH_2$—$CH_2$— (n-butylene), and mixtures thereof.

Suitable Odor Masking Agents include but are not limited to methyl acetate, ethyl acetate, cyclohexyl acetate, benzyl acetate, isoamyl acetate, geranyl acetate, hexyl acetate, octyl acetate, phenylethyl acetate, methyl butyrate, ethyl butyrate, 2-methylbutyl butyrate, isoamyl butyrate, methyl formate, methyl propionate, pentyl butyrate, 2-methylbutyl 2-methylbutyrate, ethyl methylphenylglycidate, dimethyl phthalate, or diethyl malonate.

Suitable Odor Masking Agents include but are not limited to: citral, citronellol, camphor, cedrene, carvone, dipentene, eucalyptol, geraniol, α-ionone, linalool, limonene, menthol, myrcene, neral, nerolidol, α-pinene, β-pinene, α-phellandrene, phellandrene, terpineol, α-terpinene, β-terpinene, or thujone.

Suitable Odor Masking Agents include but are not limited to: acetaldehyde, anisic aldehyde, benzaldehyde, butyraldehyde, cinnamaldehyde, capraldehyde, cuminaldehyde, decanal, hexanal, hexyl cinnamaldehyde, isomenthone, isovaleraldehyde, menthone, propionaldehyde or valeraldehyde.

Suitable Odor Masking Agents include but are not limited to: benzyl alcohol, cis-3-hexen-1-ol, furaneol, 1-hexanol, phenylethyl alcohol; 4-allylanisole, anisole, anethole, eugenol, γ-decalactone, γ-nonalactone, thymol dihydrojasmone, vanillin, mint, oil Japanese cherry or lactones In one embodiment, the Odor Masking Agent is chosen from at least one of Isoamyl butyrate, 4-Allylanisole, Limonene, Terpineol, terpenes, 4-(2,6,6-Trimethyl-2-cyclohexenyl)-3-buten-2-one, Benzaldehyde, Diethyl Malonate, Cyclohexyl acetate, Anisole, α-Ionone, mint, oil Japanese cherry and rose ketones. In one embodiment, the Odor Masking Agent is isoamyl butyrate. In some embodiments, an amount of less than 5 wt % (by total weight of composition) of odor masking agent is added to the composition. In some embodiments, an amount of less than 3 wt % (by total weight of composition) of odor masking agent is added to the composition. In some embodiments, an amount of less than 2 wt % (by total weight of composition) of odor masking agent is added to the composition. In some embodiments, an amount of less than 1 wt % (by total weight of composition) of odor masking agent is added to the composition. In some embodiments, an amount of less than about 1.6 wt % (by total weight of composition) of odor masking agent is added to the composition. In some embodiments, an amount of from 1 wt % to 3 wt % of the odor masking agent (for example, isoamyl butyrate) is added to the liquid formulations of the present invention. These formulations are imparted with stability in assay, flash point, and cold temperature for up to 12 weeks at room temperature and 45° C. The overall odor of the liquid compositions containing DMSO, for example, were significantly improved.

Examples of suitable dyes include but are not limited to any one or more of: Carbon Black, Pigment Blue 15, Pigment Blue 15:1, Pigment Blue 15:2, Pigment Blue 15:3, Pigment Blue 15:4, Pigment Blue 15:6, Pigment Blue 1, Pigment Blue 10, Pigment Blue 14, Pigment Blue 60, Pigment Blue 61, Pigment Yellow 1, Pigment Yellow 3, Pigment Yellow 12, Pigment Yellow 13, Pigment Yellow 14, Pigment Yellow 17, Pigment Yellow 24, Pigment Yellow 55, Pigment Yellow 62, Pigment Yellow 63, Pigment Yellow 65, Pigment Yellow 73, Pigment Yellow 74, Pigment Yellow 81, Pigment Yellow 83, Pigment Yellow 93, Pigment Yellow 95, Pigment Yellow 97, Pigment Yellow 110, Pigment Yellow 111, Pigment Yellow 123, Pigment Yellow 126, Pigment Yellow 127, Pigment Yellow 139, Pigment Yellow 147, Pigment Yellow 150, Pigment Yellow 151, Pigment Yellow 154, Pigment Yellow 155, Pigment Yellow 168, Pigment Yellow 170, Pigment Yellow 174, Pigment Yellow 175, Pigment Yellow 176, Pigment Yellow 179, Pigment Yellow 180, Pigment Yellow 183, Pigment Yellow 185, Pigment Yellow 188, Pigment Yellow 191, Pigment Yellow 194, Pigment Yellow 214, Pigment Red 2, Pigment Red 3, Pigment Red 4, Pigment Red 5, Pigment Red 8, Pigment Red 9, Pigment Red 12, Pigment Red 13, Pigment Red 21, Pigment Red 22, Pigment Red 23, Pigment Red 31, Pigment Red 32, Pigment Red 48:1, Pigment Red 48:2, Pigment Red 48:3, Pigment Red 48:4, Pigment Red 49:1, Pigment Red 49:2, Pigment Red 52:1, Pigment Red 52:2, Pigment Red 53:1, Pigment Red 53:3, Pigment Red 57:1, Pigment Red 63:1, Pigment Red 81, Pigment Red 112, Pigment Red 122, Pigment Red 123, Pigment Red 144, Pigment Red 146, Pigment Red 149, Pigment Red 166, Pigment Red 169, Pigment Red 170, Pigment Red 171, Pigment Red 175, Pigment Red 176, Pigment Red 177, Pigment Red 178, Pigment Red 179, Pigment Red 184, Pigment Red 185, Pigment Red 188, Pigment Red 189, Pigment Red 202, Pigment Red 208, Pigment Red 210, Pigment Red 224. Pigment Red 242, Pigment Red 245, Pigment Red 254, Pigment Red 266, Pigment Red 268, Pigment Red 269, Pigment Orange 5, Pigment Orange 13, Pigment Orange 16, Pigment Orange 34, Pigment Orange 36, Pigment Orange 63, Pigment Violet 1, Pigment Violet 2, Pigment Violet 3, Pigment Violet 19, Pigment Violet 23, Pigment Violet 27, Pigment Green 7, Pigment Green 36, and the like. Suitable dyes include but are not limited to Yellow #5 Aluminum dye lake (SunCROMA), LITHOL Fast Yellow 0991K (BASF); PALIOTOL Yellow 1840 (BASF); NOVOPERM Yellow FGL (Clariant); FD&C Yellow 5 Al Lake (SunCROMA), PALIOGEN Violet 5100 (BASF); PALIOGEN Violet 5890 (BASF); HELIOGEN Green L8730 (BASF); LITHOL Scarlet D3700 (BASF); SUNFAST Blue 15:4 (Sun Chemical); Permanent Red P-F7RK; Hostaperm Violet BL (Clariant); LITHOL Scarlet 4440 (BASF); Bon Red C (Dominion Color Company); ORACET Pink RF (BASF); PALIOGEN Red 3871K (BASF); NEOPEN Blue FF4012 (BASF); PV Fast Blue B2GO1 (Clariant); IRGALITE Blue BCA (BASF); SUNFAST Blue 15:3 (Sun Chemical); PALIOGEN Red 3340 (BASF); SUNFAST Carbazole Violet 23 (Sun Chemical); LITHOL Fast Scarlet L4300 (BASF); SUNBRITE Yellow 17 (Sun Chemical); HELIOGEN Blue L6900, L7020 (BASF); SUNBRITE Yellow 74 (Sun Chemical); SPECTRA PAC C Orange 16 (Sun Chemical); Hostaperm Blue B2G-D (Clariant); HELIOGEN Blue K6902, K6910 (BASF); SUNFAST Magenta 122 (Sun Chemical); HELIOGEN Blue D6840, D7080 (BASF); Sudan Blue OS (BASF); PALIOGEN Blue 6470 (BASF); Tartrazine yellow dye (ORCO), Sudan Orange G (Aldrich), Sudan Orange 220 (BASF); Milliken Liquitint Agro Green ZA 6040, Milliken Green #6-Experimental Green MM04201703A, Milliken Green #7-Experimental Green MM01201724A, ORCO Blue SI-MC/ORCO Yellow, PALIOGEN Orange 3040 (BASF); PALIOGEN Yellow 152, 1560 (BASF); Lumogen Yellow D0790 (BASF); Suco-Yellow L1250 (BASF); Suco-Yellow D1355 (BASF); Suco Fast Yellow DI 355, DI 351 (BASF); HOSTAPERM Pink E 02 (Clariant); Hansa Brilliant Yellow 5GX03 (Clariant); Permanent Yellow GRL 02 (Clariant); Permanent Rubine L6B 05 (Clariant); FANAL Pink D4830 (BASF); CINQUASIA Magenta (DU PONT); PALIOGEN Black L0084 (BASF); Pigment Black K801 (BASF); and carbon blacks such as REGAL 330™ (Cabot), Carbon Black 5250, Carbon Black 5750 (Columbia Chemical), as well as mixtures thereof and the like. In other embodiments, additional components, such as odor masking agents can be added to the composition.

In one embodiment, the dye is present in the composition at a lower range of about 0.05%, or 0.1%, or 0.15%, or 0.2%, or 0.25%, or 0.3%, or 0.35%, or 0.4% by weight of the composition. In one embodiment, the dye is present in the composition at a lower range of about 0.1%, or 0.2%, or 0.3%, or 0.4%, or 0.5%, or 0.6%, or 0.7%, or 0.8%, or 1% by weight of the composition.

In one embodiment, the dye is present in the composition at an upper range of about 0.8%, or 0.9%, or 1%, or 1.1%, or 1.2%, or 1.3% by weight of the composition. In one embodiment, the dye is present in the composition at an upper range of about 1%, or 2%, or 3%, or 4%, or 5% by weight of the composition.

In one embodiment, the inhibitor composition of the present invention comprises, based upon total weight of the composition:
from about 4 wt % to about 60 wt %, more typically from about 10 wt % to about 55 wt %, which in one embodiment is NBPT;
from about 55 wt % to about 96 wt %, more typically from about 58 wt % to about 90 wt %, and even more typically from about 60 wt % to about 80 wt % of at least one organic solvent;
from about 0.1 wt % to about 20 wt %, more typically from about 1 wt % to about 10 wt %, even more typically from about 1 wt % to about 5 wt % of at least one amine stabilizer and
from about 0.01 wt % to about 8 wt %, more typically from about 0.1 wt % to about 5 wt %, even more typically from about 0.1 wt % to about 3 wt % of at least one dye.

In one embodiment, the inhibitor composition of the present invention comprises, based upon total weight of the composition, from about 0.1 wt % to about 20 wt %, more typically from about 1 wt % to about 10 wt %, even more typically from about 1 wt % to about 5 wt % of at least one amine stabilizer; and In one embodiment, the inhibitor composition of the present invention comprises, based on 100 parts by weight ("pbw") of the composition:
from about 4 to about 60 pbw, more typically from about 10 to about 55 pbw, and even more typically from about 20 to about 40 pbw of a urease inhibitor, which in one embodiment is NBPT;
from about 55 to about 96 pbw, more typically from about 58 to about 90 pbw, and even more typically from about 60 to about 80 pbw of the organic solvent;
from about 0.5 to about 20 pbw, more typically from about 1 to 10 pbw, even more typically from about 1 to about 5 pbw of the amine stabilizer; and from about 0.01 to about 8 pbw, more typically from about 0.1 to 5 pbw, even more typically from about 0.1 to about 3 pbw of the dye.

In one embodiment, the inhibitor composition of the present invention comprises one or more urease inhibitors, such as, for example, NBPT or ammonium thiosulfate. In one embodiment, the inhibitor composition as described herein comprises one or more nitrification inhibitors, such as, for example DCD.

The nitrogenous fertilizer compound is treated with the inhibitor composition by contacting the nitrogenous fertilizer composition with the inhibitor composition described herein (e.g., nitrification inhibitor or urease inhibitor or a combination of both). The nitrogenous fertilizer composition may be in solid or liquid form.

Suitable nitrogenous fertilizers are those containing a nitrogenous compound such as urea, nitrate salts, ammonium salt, or a mixture thereof, such as ammonium nitrate, ammonium sulfate, ammonium thiosulfate, ammonium polysulfide, ammonium phosphates, ammonium chloride, ammonium bicarbonate, anhydrous ammonia, calcium nitrate, nitrate soda, calcium cyanamide. In one embodiment, the nitrogenous fertilizer comprises ammonium nitrate. Suitable ammonium nitrate-containing fertilizers include, for example, UAN 18, UAN 28, and UAN 30.

In one embodiment, the nitrogenous fertilizer composition is in solid particulate form, and the contacting of the nitrogenous fertilizer composition with the inhibitor composition is conducted by, for example, spraying the composition of the present invention on the particles of solid fertilizer composition.

Methods of stabilizing a liquid fertilizer composition comprise contacting 1) an amine stabilizer as described herein with 2) a liquid inhibitor composition that comprises one or more nitrogenous fertilizer compounds and at least one of a dicyandiamide or an alkyl thiophosphoric triamide, which is dissolved or dispersed in a liquid medium. The liquid medium, in some embodiments comprise: dimethylfulfoxide and at least one co-solvent selected from: (a) a dioxolane compound of formula (II.b) [described above], (b) at least one compound of formula (III) [described above], (c)

at least one compound according to formula (I.a) [described above], or (d) a glycol or glycol derivative In one embodiment, the concentrated fertilizer composition of the present invention is a solid nitrification-inhibited fertilizer composition that comprises, based on 100 pbw of the composition:

from about 60 pbw to about 99.999, more typically from about 70 pbw to about 99.999, and even more typically from about 80 pbw to about 99.999 solid particles of one or more nitrogenous fertilizer compounds, and from about 0.001 to about 40 pbw, more typically from about 0.001 to about 30 pbw, and even more typically from about 0.001 to about 20 pbw, a urease inhibitor or a nitrification inhibitor.

In one embodiment, the solid nitrification-inhibited fertilizer composition of the present invention further comprises one or more urease inhibitors, more typically NBPT.

In one embodiment, the fertilizer compound is in liquid form and the contacting of the fertilizer composition with the inhibitor composition is conducted by mixing the inhibitor composition with the liquid fertilizer composition.

In one embodiment, the concentrated fertilizer composition of the present invention is a concentrated liquid nitrification-inhibited fertilizer composition that comprises, based on 100 pbw of the composition:

from about 20 to about 99.989 pbw, more typically from about 30 to about 99.985 pbw, and even more typically from about 40 to about 99.98 pbw of one or more nitrogenous fertilizer compounds, from about 0.001 to 40 pbw, more typically from about 0.005 to 30 pbw, and even more typically from about 0.01 to 20 pbw urease inhibitor (e.g., NBPT), a nitrification inhibitor (e.g., DCD) or a combination thereof (e.g., NBPT in combination with DCD), and from about 0.01 to 60 pbw, more typically from about 0.01 to about 40 pbw, and even more typically from about 0.01 to about 30 pbw of the organic solvent or solvent mixture, as described herein.

In one embodiment, the concentrated liquid nitrification-inhibited fertilizer composition of the present invention further comprises one or more urease inhibitors, more typically NBPT.

In one embodiment, the end use fertilizer composition of the present invention is made by combining the inhibitor composition of the present invention with a concentrated nitrogenous fertilizer to form a concentrated liquid nitrification-inhibited fertilizer composition and subsequently diluting the concentrated liquid nitrification-inhibited fertilizer composition with an aqueous medium, typically water in a ratio of up to about 500 pbw, more typically from about 10 to about 500 pbw and even more typically from about 100 to about 300 pbw, of the aqueous medium per 1 pbw concentrated liquid nitrogenous fertilizer composition.

In one embodiment, the end use fertilizer composition of the present invention is made by combining the inhibitor composition of the present invention, a solid or concentrated liquid nitrogenous fertilizer, and an aqueous medium.

In one embodiment, the end use fertilizer composition of the present invention comprises one or more urease inhibitors, more typically NBPT, alone or in combination with the nitrification inhibitor.

In one embodiment, the end use fertilizer composition of the present invention comprises from about 0.001 to about 5 pbw, more typically from about 0.01 to about 2 pbw urease inhibitor and/or nitrification inhibitor per 100 pbw of the one or more nitrogenous fertilizer compounds.

In one embodiment, the end use fertilizer composition is applied to target plants or to an environment for the target plants, i.e., to ground on or within which the target plants are growing or to be grown, at a rate of from about 0.01 pounds to about 5 pounds of the fertilizer composition, more typically from about 0.05 pounds to about 2 pounds of the fertilizer composition, per 100 square feet of ground.

In one embodiment, the end use fertilizer composition is applied to target plants or to an environment for the target plants at a rate effective to provide a dosage of nitrogenous fertilizer compound of from about 0.01 pounds to about 5 pounds of fertilizer compound, more typically from about 0.05 pounds to 2 pounds of fertilizer compound, per 100 square feet of ground.

In one embodiment, the end use fertilizer composition is applied to target plants or to an environment for the target plants at a rate effective to provide a dosage of fertilizer of from about 0.01 pounds to 5 pounds of fertilizer, more typically from about 0.05 pounds to 2 pounds of fertilizer, per 1000 square feet of ground.

The composition of the present invention provides improved ease of handling of urease inhibitors and/or nitrification inhibitors, improved solubility characteristics, low toxicity of the organic solvents; good storage characteristics, and excellent miscibility with aqueous compositions, such as aqueous nitrogenous fertilizer formulations.

In one embodiment the composition comprises, by weight of composition, greater than 50 wt % of a urease inhibitor (e.g., NBPT), nitrification inhibitor (e.g., DCD), or a combination thereof, the remainder being at least solvent or a mixture of solvents, amine stabilizer and a dye. By way of example, in one embodiment, the fertilizer composition comprises, by weight of composition:

at least 50 wt % of a urease inhibitor (e.g., NBPT), nitrification inhibitor (e.g., DCD), or a combination thereof and less than or equal to 50 wt % of a solvent blend, at least one amine stabilizer and, optionally, a dye.

In one embodiment the composition comprises, by weight of composition, greater than 25 wt % of a urease inhibitor (e.g., NBPT), nitrification inhibitor (e.g., DCD), or a combination thereof, the remainder being at least solvent or a mixture of solvents, amine stabilizer and a dye. By way of example, in one embodiment, the fertilizer composition comprises, by weight of composition:

at least 25 wt % of a urease inhibitor (e.g., NBPT), nitrification inhibitor (e.g., DCD), or a combination thereof and less than or equal to 75 wt % of a solvent blend, at least one amine stabilizer and, optionally, a dye. In one embodiment, the solvent blend comprises DMSO.

In one embodiment the stable liquid agricultural composition comprises, by weight of composition, greater than 25 wt % of a urease inhibitor;

a solvent blend comprising a) a mixture of triethylene glycol and b) at least one compound of formula (III):

$$R_3OOC\text{-}A\text{-}CONR_4R_5 \quad (III),$$

wherein $R_3$ comprises a $C_1$-$C_{36}$ alkyl group; wherein $R_4$ and $R_5$ individually comprise a $C_1$-$C_{36}$ alkyl group, wherein $R_4$ and $R_5$ can optionally together form a ring; and wherein A is a linear or a branched divalent $C_2$-$C_{12}$ alkyl group; and optionally, a dye In one embodiment the stable liquid agricultural composition comprises, by weight of composition, greater than 25 wt % of a urease inhibitor;

a solvent blend comprising a) a mixture of triethylene glycol and b) propylene glycol; and
optionally, a dye.

In one embodiment the stable liquid agricultural composition comprises, by weight of composition:
less than 30 wt % of a urease inhibitor;
a solvent blend comprising a) a glycol derivative and b) at least one compound of formula (III):

$$R_3OOC\text{-}A\text{-}CONR_4R_5 \quad (III),$$

wherein $R_3$ comprises a $C_1$-$C_{36}$ alkyl group; wherein $R_4$ and $R_5$ individually comprise a $C_1$-$C_{36}$ alkyl group, wherein $R_4$ and $R_5$ can optionally together form a ring; and wherein A is a linear or a branched divalent $C_2$-$C_{12}$ alkyl group;
optionally, a dye; and
optionally, an odor masking agent.

In one embodiment, the glycol derivative is triethylene glycol.

In one embodiment the stable liquid agricultural composition comprises, by weight of composition:
less than 30 wt % of a urease inhibitor;
a solvent blend comprising a mixture of glycol derivatives;
optionally, a dye; and
optionally, an odor masking agent.

The mixture of glycol derivatives can comprise, in one embodiment, triethylene glycol and propylene glycol.

In one embodiment the composition comprises, by weight of composition, greater than 50 wt % of a urease inhibitor such as NBPT, the remainder being solvent or a mixture of solvents with the amine stabilizer. In one embodiment the composition comprises, by weight of composition, greater than 51 wt %, 52 wt %, 53 wt %, 54 wt % of a urease inhibitor such as NBPT, the remainder being solvent or a mixture of solvents with the amine stabilizer. In one embodiment the composition comprises, by weight of composition, greater than 55 wt %, 56 wt %, 57 wt %, 58 wt %, 59 wt % a urease inhibitor such as of NBPT, the remainder being solvent or a mixture of solvents with the amine stabilizer. In one embodiment the composition comprises, by weight of composition, greater than 60 wt % of a urease inhibitor such as NBPT, the remainder being solvent or a mixture of solvents with the amine stabilizer. In one embodiment the composition comprises, by weight of composition, greater than 65 wt % of a urease inhibitor such as NBPT, the remainder being solvent or a mixture of solvents with the amine stabilizer. In one embodiment the composition comprises, by weight of composition, greater than 70 wt % of a urease inhibitor such as NBPT, the remainder being solvent or a mixture of solvents with the amine stabilizer. In one embodiment the composition comprises, by weight of composition, greater than 75 wt % of a urease inhibitor such as NBPT, the remainder being solvent or a mixture of solvents with the amine stabilizer.

In one embodiment the composition comprises, by weight of composition, greater than 50 wt % of a nitrification inhibitor such as DCD, the remainder being solvent or a mixture of solvents with the amine stabilizer. In one embodiment the composition comprises, by weight of composition, greater than 51 wt %, 52 wt %, 53 wt %, 54 wt % of a nitrification inhibitor such as DCD, the remainder being solvent or a mixture of solvents with the amine stabilizer. In one embodiment the composition comprises, by weight of composition, greater than 55 wt %, 56 wt %, 57 wt %, 58 wt %, 59 wt % of a nitrification inhibitor such as DCD, the remainder being solvent or a mixture of solvents with the amine stabilizer. In one embodiment the composition comprises, by weight of composition, greater than 60 wt % of a nitrification inhibitor such as DCD, the remainder being solvent or a mixture of solvents with the amine stabilizer. In one embodiment the composition comprises, by weight of composition, greater than 65 wt % of a nitrification inhibitor such as DCD, the remainder being solvent or a mixture of solvents with the amine stabilizer. In one embodiment the composition comprises, by weight of composition, greater than 70 wt % of a nitrification inhibitor such as DCD, the remainder being solvent or a mixture of solvents with the amine stabilizer. In one embodiment the composition comprises, by weight of composition, greater than 75 wt % of a nitrification inhibitor such as DCD, the remainder being solvent or a mixture of solvents with the amine stabilizer.

In one embodiment the composition comprises, by weight of composition, greater than 30 wt % of DCD and/or NBPT, the remainder being solvent or a mixture of solvents with the amine stabilizer and dye. By way of example, in one embodiment, the fertilizer composition comprises, by weight of composition, 20-30 wt % of NBPT and 70-80 wt % of a solvent blend of: (i) at least one dioxolane compound of formula (II.b):

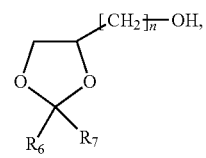

wherein $R_6$ and $R_7$ individually comprises a hydrogen, an alkyl group, an alkenyl group, or a phenyl group, wherein n is an integer of from 1 to 10.

In one embodiment the composition comprises, by weight of composition, greater than 40 pbw of NBPT (or NBPT in combination with DCD), the remainder being solvent or a mixture of solvents.

In one embodiment the composition comprises, by weight of composition, greater than 50 pbw of NBPT (or NBPT in combination with DCD), the remainder being solvent or a mixture of solvents.

EXPERIMENTS

Experiment 1—2-Amino-2-methyl-1-propanol

Compositions were prepared by mixing components in the amounts indicated in Table 1. The amine stabilizer utilized was 2-Amino-2-methyl-1-propanol. Composition 1 was utilized as a comparative example, i.e., without added amine stabilizer.

Table 1. Various Compositions with/without 2-Amino-2-methyl-1-propanol

TABLE 1

Various Compositions with/without 2-Amino-2-methyl-1-propanol

| Component | Composition 1 wt % | Composition 2 wt % | Composition 3 wt % |
|---|---|---|---|
| NBPT | 52 | 52 | 52 |
| DMSO | 48 | 44 | 38 |

TABLE 1-continued

Various Compositions with/without
2-Amino-2-methyl-1-propanol

| Component | Composition 1 wt % | Composition 2 wt % | Composition 3 wt % |
| --- | --- | --- | --- |
| 2-Amino-2-methyl-1-propanol | 0 | 4 | 10 |
| Total | 100 | 100 | 100 |

Table 2. Flash point of Compositions (2-Amino-2-methyl-1-propanol)

TABLE 2

Flash point of Compositions
(2-Amino-2-methyl-1-propanol)

| NBPT + DMSO with 2-Amino-2-methyl-1-propanol (wt %) | Initial flash point (° C.) | Flash point after 2 weeks at 54° C. (° C.) |
| --- | --- | --- |
| 0 | 96.5 | 52.0 |
| 4% | 92.1 | 90.3 |
| 10% | 89.3 | 89.2 |

Referring to Table 2, the flash point was measured for Composition 1 (control), Composition 2 and Composition 3 initially and 2 weeks thereafter. Without an amine stabilizer, the flash point of the NBPT composition (i.e., Composition 1) exhibited a dramatic drop from 96.5° C. to 52.0 after 2 weeks at 54° C. The solution was observed to undergo a color change from colorless, initially, to dark brown with a noticeable amount of sediments after 2 weeks at 54° C. The flash point of NBPT composition with 4% 2-Amino-2-methyl-1-propanol (Composition 2) is stable at around 90° C. after two weeks at 54° C. The sedimentation was observed to be dramatically reduced as compared to the control. The flash point of the NBPT composition with 10% 2-Amino-2-methyl-1-propanol (Composition 3) is stable at around 89.2° C. after two weeks at 54° C. Upon observation, only a slight change in the color of the solution and almost no sedimentation was observed.

Experiment 2—Amino-2-propanol

Compositions were prepared by mixing components in the amounts indicated in Table 3. The amine stabilizer utilized was Amino-2-propanol. Composition 1a was utilized as a comparative example, i.e., without added amine stabilizer.

TABLE 3

Various Compositions with/without Amino-2-propanol

| Component | Composition 1a wt % | Composition 2a wt % | Composition 3a wt % |
| --- | --- | --- | --- |
| NBPT | 52 | 52 | 52 |
| DMSO | 48 | 44 | 38 |
| Amino-2-propanol | 0 | 4 | 10 |
| Total | 100 | 100 | 100 |

TABLE 4

Flash point of Compositions with Amino-2-propanol

| NBPT + DMSO with Amino-2-propanol (wt %) | Initial flash point (° C.) | Flash point after 2 weeks at 54° C. (° C.) |
| --- | --- | --- |
| 0 | 96.5 | 52.0 |
| 4% | 92.2 | 69.6 |
| 10% | 88.2 | 75.0 |

Referring to Table 4, the flash point was measured for Composition 1a (control), Composition 2a and Composition 3a initially and 2 weeks thereafter. Without an amine stabilizer, the flash point of the NBPT composition (i.e., Composition 1a) exhibited a dramatic drop from 96.5° C. to 52.0 after 2 weeks at 54° C. The drop in the flash point of the NBPT composition decreases significantly by adding 10% Amino-2-propanol (Composition 3a). It was observed that the addition of the amine stabilizer, Amino-2-propanol, in Compositions 2a and 3a also reduces sediments in the solution versus the control.

Experiment 3—2-Amino-1-butanol

Compositions were prepared by mixing components in the amounts indicated in Table 5. The amine stabilizer utilized was 2-Amino-1-butanol. Composition 1b was utilized as a comparative example, i.e., without this added amine stabilizer.

TABLE 5

Composition with/without 2-Amino-1-butanol

| Component | Composition 1b wt % | Composition 2b wt % | Composition 3b wt % |
| --- | --- | --- | --- |
| NBPT | 52 | 52 | 52 |
| DMSO | 48 | 44 | 38 |
| 2-Amino-1-butanol | 0 | 4 | 10 |
| Total | 100 | 100 | 100 |

TABLE 6

Flash point of Compositions with 2-Amino-1-butanol

| NBPT + DMSO with 2-Amino-1-butanol (wt %) | Initial flash point (° C.) | Flash point after 2 weeks at 54° C. (° C.) |
| --- | --- | --- |
| 0 | 96.5 | 52.0 |
| 4% | 94.1 | 91.5 |
| 10% | 93.2 | 92.6 |

Referring to Table 6, the flash point was measured for Composition 1b (control), Composition 2b and Composition 3b initially and 2 weeks thereafter. Without the 2-Amino-1-butanol amine stabilizer, the flash point of the control (Composition 1b) exhibited a dramatic drop from 96.5° C. to 52.0 after 2 weeks at 54° C. The solution was observed to undergo a color change from colorless to dark brown and produces large amounts of sediments after 2 weeks at 54° C. The flash point of the NBPT composition with 4% 2-Amino-1-butanol (Composition 2b) is stable at 91.5° C. after two weeks at 54° C. Sedimentation was observed to be dramatically reduced versus the control. The flash point of NBPT composition with 10% 2-Amino-1- butanol (Composition 3b) is stable at 92.6° C. after two weeks at 54° C. Only a slight change in the color of the solution and almost no sedimentation was observed in solution.

Experiment 4—Amine stabilizer for NBPT+DCD (2-Amino-2-methyl-1-propanol)

TABLE 7

Composition of NBPT + DCD with 2-Amino-2-methyl-1-propanol

| Component | Composition 1c wt % | Composition 2c wt % |
|---|---|---|
| NBPT | 6 | 6 |
| DCD | 24 | 24 |
| DMSO | 70 | 68 |
| 2-Amino-2-methyl-1-propanol | 0 | 2 |
| Total | 100 | 100 |

Summary of Observations:

The color of solution of the NBPT and DCD composition (Composition 1c) changes from colorless to amber after 2 weeks at 54° C. The color of solution of the NBPT and DCD composition does not change with the addition of 2% 2-Amino-2-methyl-1-propanol (Composition 2c) after 2 weeks at 54° C. This would appear to indicate that Composition 2c is more stable (degradation stability) over the same period of time versus the control.

Experiment 5—Amine stabilizer for NBPT+DCD—Amino-2-propanol

TABLE 8

Composition of NBPT + DCD with Amino-2-propanol

| Component | Composition 1d wt % | Composition 2d wt % |
|---|---|---|
| NBPT | 6 | 6 |
| DCD | 24 | 24 |
| DMSO | 70 | 68 |
| Amino-2-propanol | 0 | 2 |
| Total | 100 | 100 |

Summary of Observations:

The color of solution of the NBPT and DCD composition (Composition 1d) changes from colorless to amber after 2 weeks at 54° C. The color of solution of the NBPT and DCD composition does not change with the addition of 2% Amino-2-propanol (Composition 2d) after 2 weeks at 54° C. This would appear to indicate that Composition 2d is more stable (degradation stability) over the same period of time versus the control.

Experiment 6—Amine stabilizer for NBPT+DCD—2-Amino-1-butanol

TABLE 9

Composition of N-Dual with 2-Amino-1-butanol

| Component | Composition 1e wt % | Composition 2e wt % |
|---|---|---|
| NBPT | 6 | 6 |
| DCD | 24 | 24 |
| DMSO | 70 | 68 |
| 2-Amino-1-butanol | 0 | 2 |
| Total | 100 | 100 |

Summary of Observations:

The color of solution of the NBPT and DCD (Composition 1e) composition changes from colorless to amber after 2 weeks at 54° C. The color of solution of the NBPT and DCD composition does not change too much with the addition of 2% 2-Amino-1-butanol (Composition 2e) after 2 weeks at 54° C.

What is claimed is:

1. A stable liquid agricultural composition comprising N-(n-butyl)-thiophosphoric triamide (NBPT) urease inhibitor, wherein between 40 and 55 wt. % of the composition is N-(n-butyl)-thiophosphoric triamide (NBPT);
dimethyl sulfoxide;
and
an amine stabilizer selected from the group consisting of 2-amino-2-methyl-1-propanol, 2-amino-1-butanol and mixtures thereof, wherein the amine stabilizer is present in an amount of from 4 wt % to about 15 wt %, by total weight of the composition;
wherein there is an absence of each and every compound according to formula (I.a):

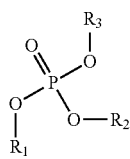

(I.a)

wherein $R_1$, $R_2$ and $R_3$, are each independently chosen from H, a $C_1$-$C_{16}$ alkyl group, a $C_1$-$C_{16}$ alkenyl, group, a $C_1$-$C_{16}$ alkoxyalkyl group, a $C_7$-$C_{30}$ alkylarylalkyl group, a $C_7$-$C_{30}$ arylalkyl group, or an aryl group, provided that at least one of $R_1$, $R_2$ and $R_3$ is not H.

2. The liquid agricultural composition of claim 1, wherein at least 38 wt. % of the composition is DMSO and the amine stabilizer is 2-amino-2-methyl-1-propanol, 2-amino-1-butanol or mixtures thereof.

3. The liquid agricultural composition of claim 1, wherein the amine stabilizer is present in an amount of from 4 wt % to about 10 wt %, by weight of composition.

4. The liquid agricultural composition of claim 1, wherein between 45 and 55 wt. % of the composition is the N-(n-butyl)-thiophosphoric triamide (NBPT) and 38 to 44 wt. % of the composition is dimethyl sulfoxide.

5. The liquid agricultural composition of claim 1, further comprising at least one nitrification inhibitor.

6. The liquid agricultural composition of claim 5, wherein the nitrification inhibitor is dicyandiamide (DCD).

7. The liquid agricultural composition of claim 1, further comprising at least one dye.

8. The liquid agricultural composition of claim 1, further comprising an odor masking agent comprising at least one of terpineol, 4-allylanisole, limonene4-(2,6,6-Trimethyl-2-cyclohexenyl)-3-buten-2-one, isoamyl butyrate, benzaldehyde, diethyl malonate, cyclohexyl acetate, anisole, mint, oil Japanese cherry, or α-Ionone.

9. The liquid agricultural composition of claim 1, wherein between 45 and 55 wt. % of the composition is the N-(n-butyl)-thiophosphoric triamide (NBPT).

10. A stable liquid agricultural composition comprising:
N-(n-butyl)-thiophosphoric triamide (NBPT) urease inhibitor, wherein between 40 and 55 wt. % of the composition is N-(n-butyl)-thiophosphoric triamide (NBPT);
an amine stabilizer selected from the group consisting of 2-amino-2-methyl-1-propanol, 2-amino-1-butanol and mixtures thereof, wherein the amine stabilizer is present in an amount of from 4 to 15 wt. %, by total weight of the composition;
dimethyl sulfoxide; and
an odor masking agent comprising at least one of terpineol, 4-allylanisole, limonene4-(2,6,6-Trimethyl-2-cyclohexenyl)-3-buten-2-one, isoamyl butyrate, benzaldehyde, diethyl malonate, cyclohexyl acetate, anisole, mint, oil Japanese cherry, or α-Ionone,
wherein there is an absence of each and every compound according to formula (I.a):

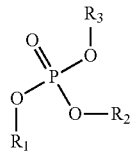

(I.a)

wherein $R_1$, $R_2$ and $R_3$, are each independently chosen from H, a $C_1$-$C_{16}$ alkyl group, a $C_1$-$C_{16}$ alkenyl, group, a $C_1$-$C_{16}$ alkoxyalkyl group, a $C_7$-$C_{30}$ alkylarylalkyl group, a $C_7$-$C_{30}$ arylalkyl group, or an aryl group, provided that at least one of $R_1$, $R_2$ and $R_3$ is not H.

11. The liquid agricultural composition of claim 10, optionally further comprising dicyandiamide (DCD) as a nitrification inhibitor, wherein the composition contains 10 to 75% total urease inhibitor and nitrification inhibitor,
wherein between 40 and 55 wt. % of the composition is the at least one urease inhibitor.

12. The liquid agricultural composition of claim 10, wherein the amine stabilizer is 2-amino-2-methyl-1-propanol.

13. The liquid agricultural composition of claim 10, wherein the amine stabilizer is 2-amino-1-butanol.

14. The liquid agricultural composition of claim 10, wherein the amine stabilizer is the mixture of 2-amino-2-methyl-1-propanol and 2-amino-1-butanol.

15. The liquid agricultural composition of claim 10, wherein the at least one urease inhibitor is present in an amount between 45 and 55 wt %, by total weight of composition.

16. The liquid agricultural composition of claim 1, wherein the N-(n-butyl)-thiophosphoric triamide (NBPT) is present in an amount between 45 and 55 wt %, by total weight of composition, and wherein 38 to 44 wt. % of the composition is DMSO.

17. The liquid agricultural composition of claim 10, wherein the at least one a urease inhibitor is present in an amount between 50 and 55 wt %, by total weight of composition.

18. The liquid agricultural composition of claim 1, wherein the amine stabilizer is present in an amount less than 50% by total weight of the liquid fertilizer composition.

19. The liquid agricultural composition of claim 1, wherein the amine stabilizer is present in an amount from 4 to 10% by total weight of the liquid fertilizer composition.

20. The liquid agricultural composition of claim 2, wherein the amine stabilizer is present in an amount from 4% to 10% by total weight of the liquid fertilizer composition.

21. The liquid agricultural composition of claim 10, further comprising at least one nitrification inhibitor.

22. The liquid agricultural composition of claim 21, wherein the nitrification inhibitor is dicyandiamide (DCD).

23. A method of making a solid or concentrated liquid fertilizer composition comprising contacting one or more nitrogenous fertilizer compounds with a liquid inhibitor composition of claim 1 that comprises between 40 and 55 wt. % N-(n-butyl)-thiophosphoric triamide (NBPT) as urease inhibitor, which is dissolved or dispersed in a liquid medium comprising:
dimethyl sulfoxide, wherein at least 38 wt. % of the composition is dimethyl sulfoxide; and
an amine stabilizer selected from the group consisting of 2-amino-2-methyl-1-propanol, 2-amino-1-butanol and any combination thereof, wherein the amine stabilizer is present in an amount of from 4 wt % to 15 wt %, by weight of composition,
wherein there is an absence of each and every compound according to formula (I.a):

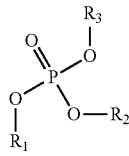

(I.a)

wherein $R_1$, $R_2$ and $R_3$, are each independently chosen from H, a $C_1$-$C_{16}$ alkyl group, a $C_1$-$C_{16}$ alkenyl, group, a $C_1$-$C_{16}$ alkoxyalkyl group, a $C_7$-$C_{30}$ alkylarylalkyl group, a $C_7$-$C_{30}$ arylalkyl group, or an aryl group, provided that at least one of $R_1$, $R_2$ and $R_3$ is not H.

24. The method of claim 23, wherein the liquid medium further comprises an odor masking agent comprising at least one of terpineol, 4-allylanisole, limonene4-(2,6,6-Trimethyl-2-cyclohexenyl)-3-buten-2-one, isoamyl butyrate, benzaldehyde, diethyl malonate, cyclohexyl acetate, anisole, mint, oil Japanese cherry, or α-Ionone.

25. The liquid agricultural composition of claim 24, wherein the amine stabilizer is 2-amino-2-methyl-1-propanol.

26. A stable liquid agricultural composition consisting of
between 40 and 55 wt. % N-(n-butyl)-thiophosphoric triamide (NBPT) as a urease inhibitor;
dimethyl sulfoxide, wherein at least 38 wt. % of the composition is dimethyl sulfoxide;

an amine stabilizer selected from the group consisting of 2-amino-2-methyl-1-propanol, 2-amino-1-butanol and mixtures thereof, wherein the amine stabilizer is present in an amount of from 4 wt % to 15 wt %, by weight of composition;

optionally, at least one nitrification inhibitor;

optionally, at least one co-solvent selected from the group consisting of:

(a) at least one dioxolane compound of formula (II.b):

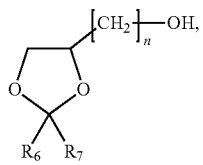

(II.b)

wherein $R_6$ and $R_7$ individually comprises a hydrogen, an alkyl group, an alkenyl group, or a phenyl group, wherein n is an integer of from 1 to 10;

b) at least one compound of formula (III):

$R_3OOC$-A-$CONR_4R_5$ (III), wherein $R_3$ comprises a $C_1$-$C_{36}$ alkyl group; wherein $R_4$ and $R_5$ individually comprise a $C_1$-$C_{36}$ alkyl group, wherein $R_4$ and $R_5$ can optionally together form a ring; and wherein A is a linear or a branched divalent $C_2$-$C_{12}$ alkyl group; and c) a glycol, or glycol derivative, or combinations thereof; and optionally, at least one dye;

optionally, an odor masking agent comprising at least one member selected from the group consisting of terpineol, 4-allylanisole, limonene4-(2,6,6-Trimethyl-2-cyclohexenyl)-3-buten-2-one, isoamyl butyrate, benzaldehyde, diethyl malonate, cyclohexyl acetate, anisole, mint, oil Japanese cherry, and α-Ionone.

27. The liquid agricultural composition of claim 26, consisting of the N-(n-butyl)-thiophosphoric triamide (NBPT) as the urease inhibitor, wherein between 45 and 55 wt. % of the composition is N-(n-butyl)-thiophosphoric triamide (NBPT);

the dimethyl sulfoxide, wherein 38 to 44 wt. % of the composition is dimethyl sulfoxide;

the amine stabilizer selected from the group consisting of 2-amino-2-methyl-1-propanol,2-amino-1-butanol and any combination thereof optionally, the at least one nitrification inhibitor;

optionally, the at least one dye.

28. The liquid agricultural composition of claim 27, wherein the amine stabilizer is 2-amino-2-methyl-1-propanol.

* * * * *